US012642799B2

(12) United States Patent
Mohapatra et al.

(10) Patent No.: US 12,642,799 B2
(45) Date of Patent: Jun. 2, 2026

(54) COMPOSITION AND METHOD FOR TREATING COVID-19

(71) Applicant: University of South Florida, Tampa, FL (US)

(72) Inventors: Subhra Mohapatra, Lutz, FL (US); Shyam S. Mohapatra, Lutz, FL (US); Karthick Mayilsamy, Tampa, FL (US); Eleni Markoutsa, Tampa, FL (US); Andrew McGill, Tampa, FL (US)

(73) Assignee: University of South Florida, Tampa, FL (US)

( * ) Notice: Subject to any disclaimer, the term of this patent is extended or adjusted under 35 U.S.C. 154(b) by 81 days.

(21) Appl. No.: 18/389,272

(22) Filed: Nov. 14, 2023

(65) Prior Publication Data

US 2024/0100047 A1     Mar. 28, 2024

Related U.S. Application Data

(63) Continuation of application No. PCT/US2022/029366, filed on May 16, 2022.

(60) Provisional application No. 63/202,897, filed on Jun. 29, 2021, provisional application No. 63/201,819, filed on May 14, 2021.

(51) Int. Cl.
| | |
|---|---|
| *A61K 31/4985* | (2006.01) |
| *A61K 9/127* | (2025.01) |
| *A61K 9/51* | (2006.01) |
| *A61K 31/155* | (2006.01) |
| *A61P 31/14* | (2006.01) |

(52) U.S. Cl.
CPC .......... *A61K 31/4985* (2013.01); *A61K 9/127* (2013.01); *A61K 9/5123* (2013.01); *A61K 31/155* (2013.01); *A61P 31/14* (2018.01)

(58) Field of Classification Search
CPC .. A61K 31/4985; A61K 9/127; A61K 9/5123; A61K 31/155; A61K 9/0053; A61P 31/14
See application file for complete search history.

(56) References Cited

U.S. PATENT DOCUMENTS

2018/0256494 A1* 9/2018 Park ...................... A61K 31/59

OTHER PUBLICATIONS

P. P. Shah et al., "Effect of oleic acid modified polymeric bilayered nanoparticles on percutaneous delivery of spantide II and ketoprofen," Journal of Controlled Release 158 (2012) 336-345.*
L. P. Bharath et al., "The intersection of metformin and inflammation," Am J Physiol Cell Physiol 320: C873-C879, 2021.*
S. Kumar et al., "Metformin-loaded alginate nanoparticles as an effective antidiabetic agent for controlled drug release," Royal Pharmaceutical Society, Journal of Pharmacy and Pharmacology, 69 (2017), pp. 143-150.*
D. Yang et al., "The antimicrobial activity of liposomal lauric acids against *Propionibacterium acnes*," Biomaterials 30 (2009) p. 6035-6040.*
J. Lee et al., "Anticancer Effect of Metformin in Herceptin-Conjugated Liposome for Breast Cancer," Pharmaceutics, vol. 12, published Dec. 20, 2019, p. 1-13.*
A. P. Desbois et al., "Antibacterial Activity of Long-Chain Poly-unsaturated Fatty Acids against *Propionibacterium acnes* and *Staphylococcus aureus*," Mar. Drugs 2013, 11, 4544-4557.*
Belanger, M.J. et al., Covid-19 and disparities in nutrition and obesity, N Engl J Med, Sep. 10, 2020, 383:11.
Ryan, P. et al., Is adipose tissue a reservoir for viral spread, immune activation, and cytokine amplification in coronavirus disease 2019?, Obesity, 2020, 0:1-4.
Mahamat-Saleh Y. et al., Diabetes, hypertension, body mass index, smoking and COVID-19 related mortality: a systematic review and meta-analysis of observational studies, BMJ Open, Oct. 2, 20215, 11(10):e052777.
Sanchis-Gomar F. et al., Obesity and outcomes in COVID-19: When an epidemic and pandemic collide, Mayo Clin Proc, 2020, 95(7):1445-1453.
Samuel, S.M. et al., Therapeutic potential of metformin in COVID-19: reasoning for its protective role, Trends in Microbiology, Oct. 2021, 29(10):894-907.
Williams, B. Renin angiotensin system inhibition as treatment for Covid-19?, EClinicalMedicine, 2021, 37:101023.
Bardaweel, S. et al., Sitagliptin: a potential drug for the treatment of COVID-19?, Acta Pharm., 2021, 71:175-184.
Dastan, F. et al., Sitagliptin repositioning in SAARS-CoV-2: effects on ACE-2, CD-26, and inflammatory cytokine storms in the lung, Iran J Allergy Asthma Immunol, May 2020, 19(Suppl. 1):10-12.
Kutsukake M., et al. Pioglitazone attenuates lung injury by modulating adipose inflammation. J Surg Res. 2014;189 (2):295-303.
Mayilsamy K., et al. Treatment with shCCL20-CCR6 nanodendriplexes and human mesenchymal stem cell therapy improves pathology in mice with repeated traumatic brain injury. Nanomedicine : nanotechnology, biology, and medicine. 2020;29:102247. Epub Jul. 1, 2020.
Matthews L., et al. Pioglitazone for Hepatic Steatosis in HIV/Hepatitis C Virus Coinfection. AIDS Res Hum Retroviruses. 2015;31(10):961-6. Epub Jul. 28, 2015.

(Continued)

*Primary Examiner* — Monica A Shin
(74) *Attorney, Agent, or Firm* — Michele L. Lawson; Shumaker, Loop & Kendrick, LLP

(57) ABSTRACT

A nanosystem and methods of treating, including prophylactically, coronavirus infections, such as those caused by severe acute respiratory syndrome coronavirus 2 (SARS-CoV-2), by administering such nanosystem to a patient is presented. The nanosystem may be comprised of a single or a combination of therapeutic agents, optionally encapsulated in a nanoparticle having a targeting moiety directed to the particular coronavirus. For CoV-2 infections, at least one therapeutic agent, such as the dual DPP4/ACE2 inhibitor sitagliptin, may optionally be encapsulated within a nanoparticle having a fatty acid such as linoleic acid, as the targeting moiety. Administration can occur intranasally prior to infection for prophylactic treatment or post-infection for treatment of the viral infection.

3 Claims, 8 Drawing Sheets

(56)  References Cited

OTHER PUBLICATIONS

Das, M. et al. Magnetic micelles for DNA delivery to rat brains after mild traumatic brain injury. Nanomedicine : nanotechnology, biology, and medicine. 2014;10(7):1539-48. Epub Feb. 4, 2014.

Arnold R, et al. Peroxisome-proliferator-activated receptor-gamma agonists inhibit the release of proinflammatory cytokines from RSV-infected epithelial cells. Virology. 2006;346(2):427-39. Epub Dec. 7, 2005.

International Search Report issued by the International Searching Authority on Oct. 5, 2022 for corresponding international patent application No. PCT/US22/29366.

International Preliminary Report on Patentability issued by the International Bureau on Oct. 11, 2023 for corresponding international patent application No. PCT/US22/29366.

* cited by examiner

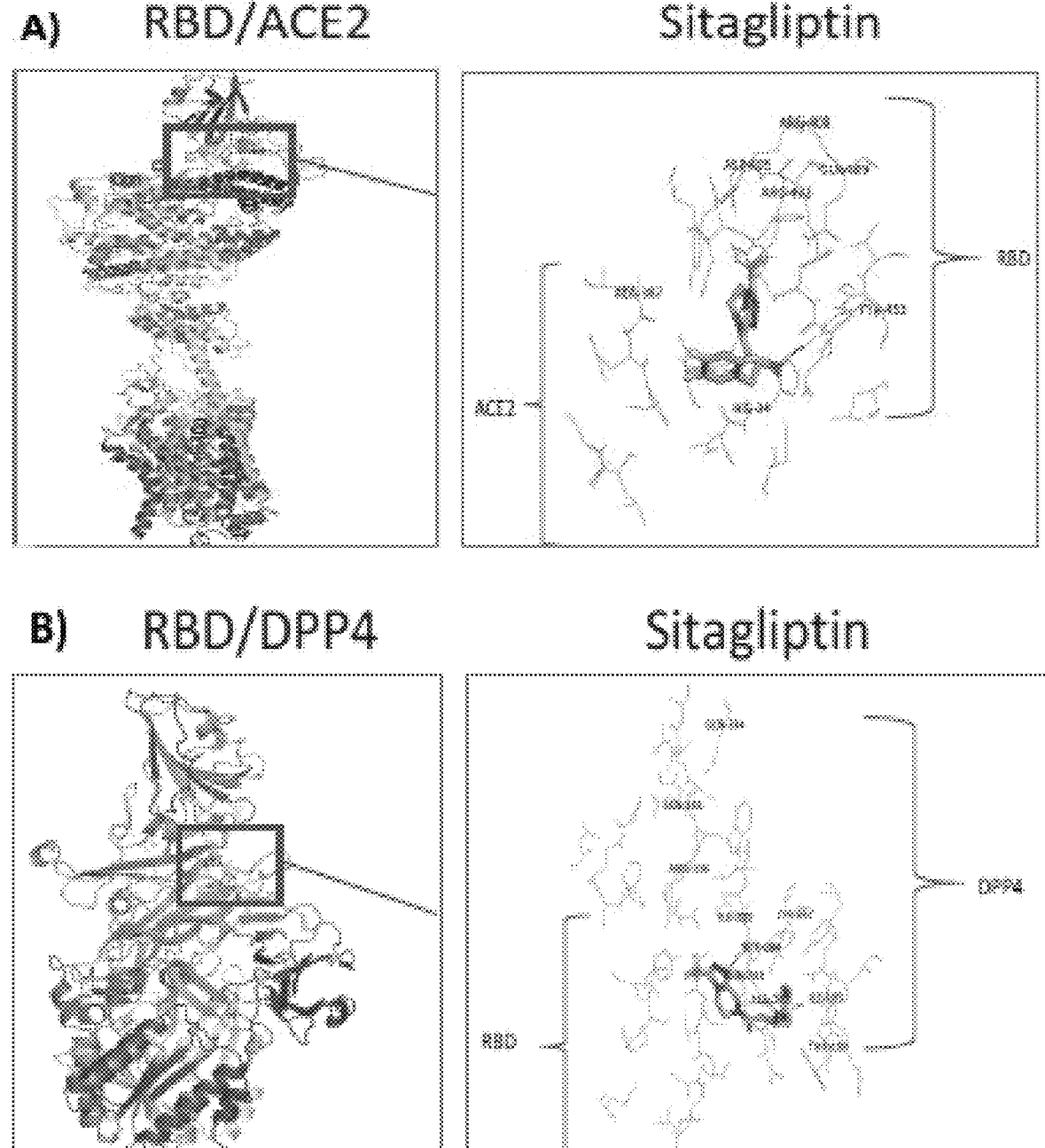
FIG. 1A-B

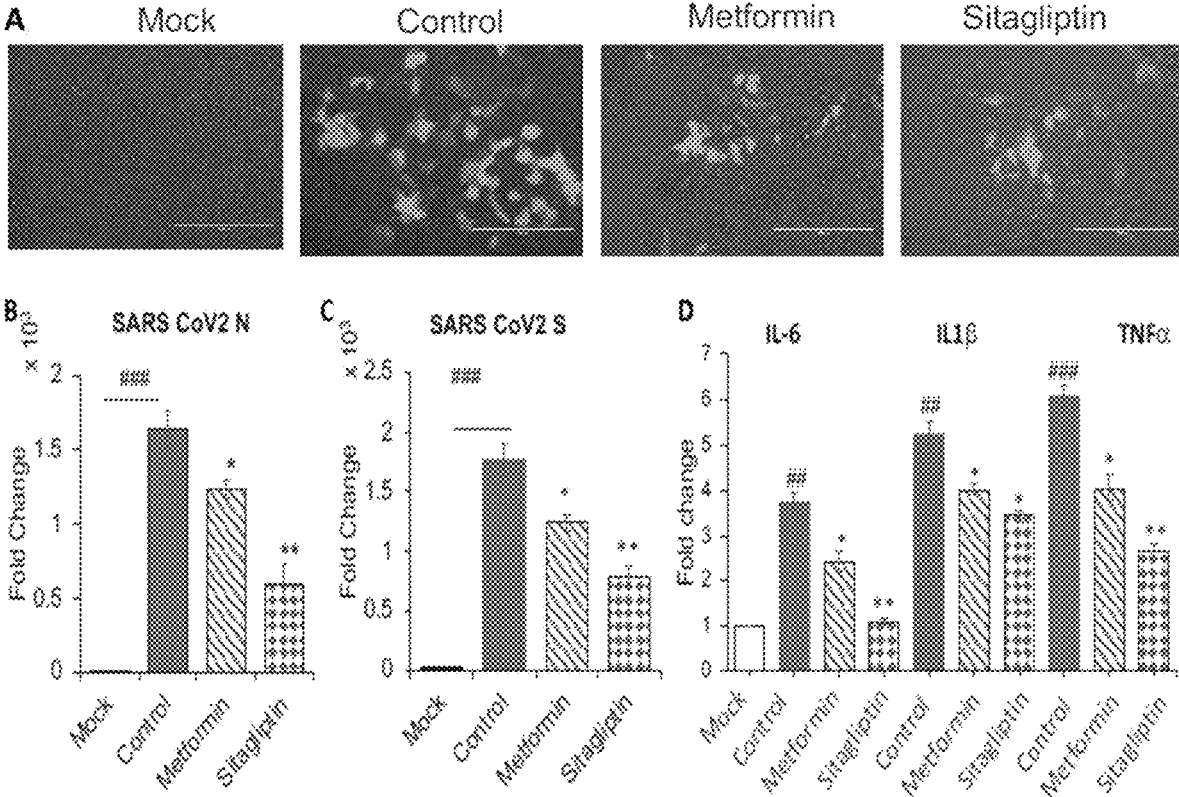
FIG. 2A-D

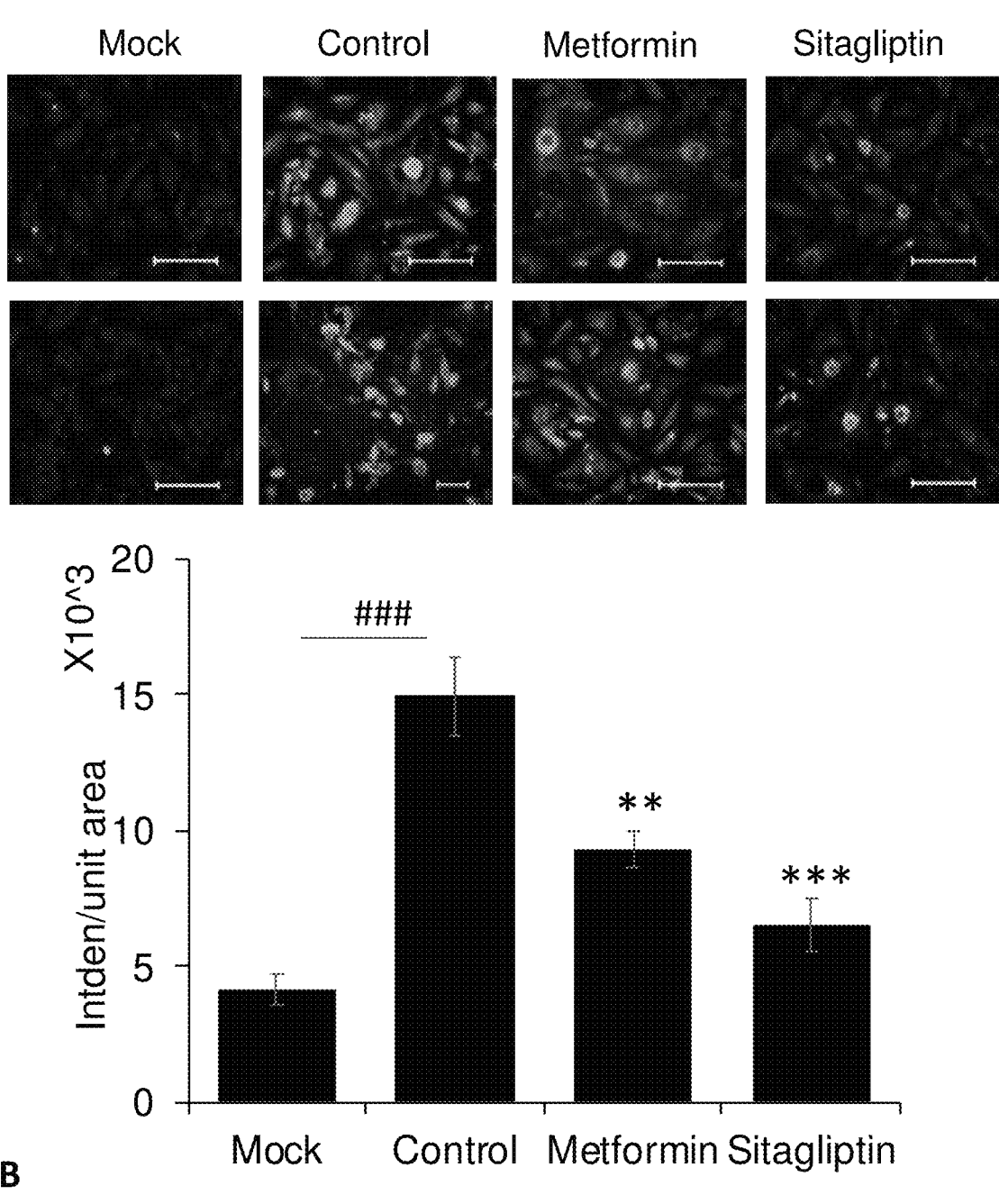
FIG. 3A-B

C

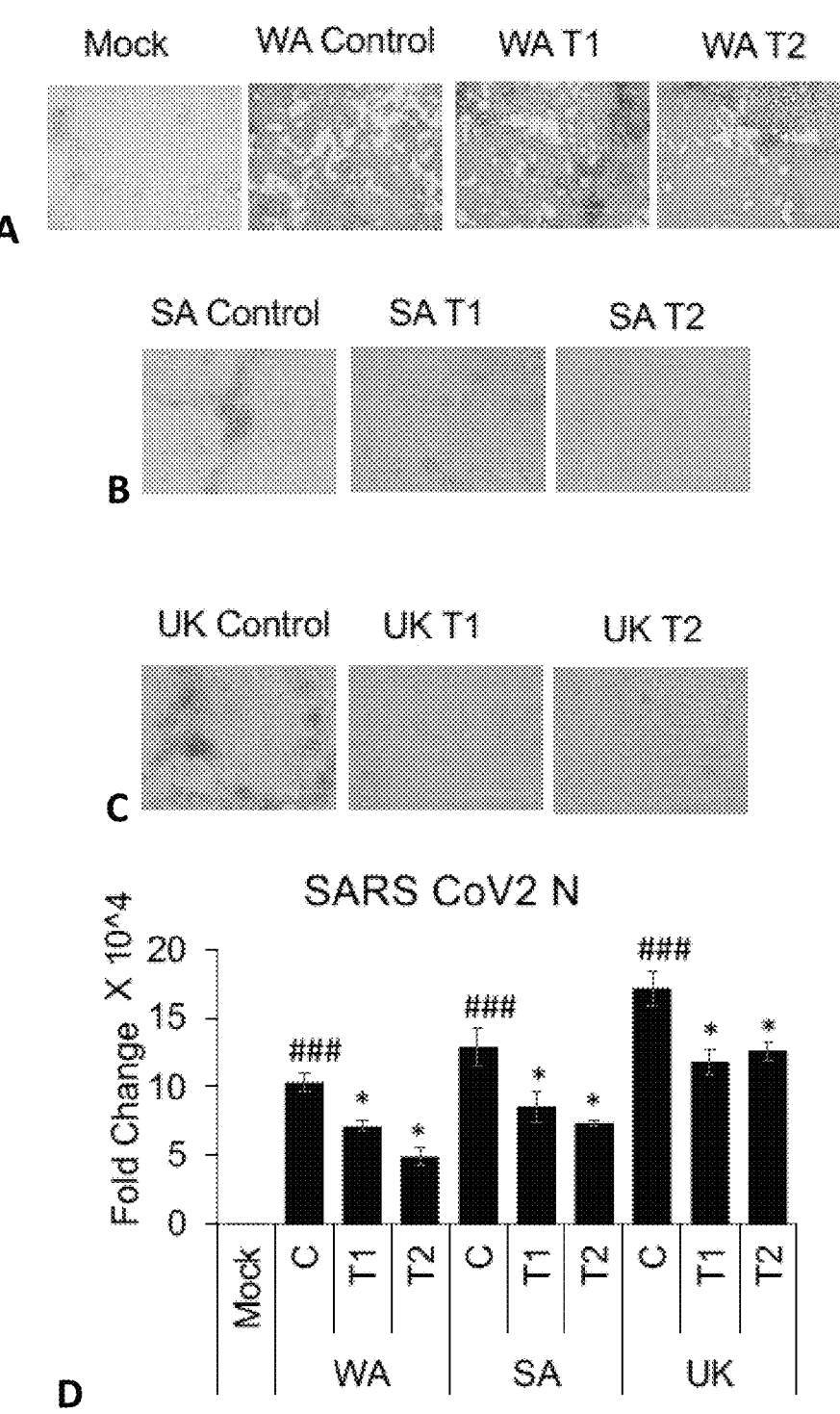
FIG. 4A-D

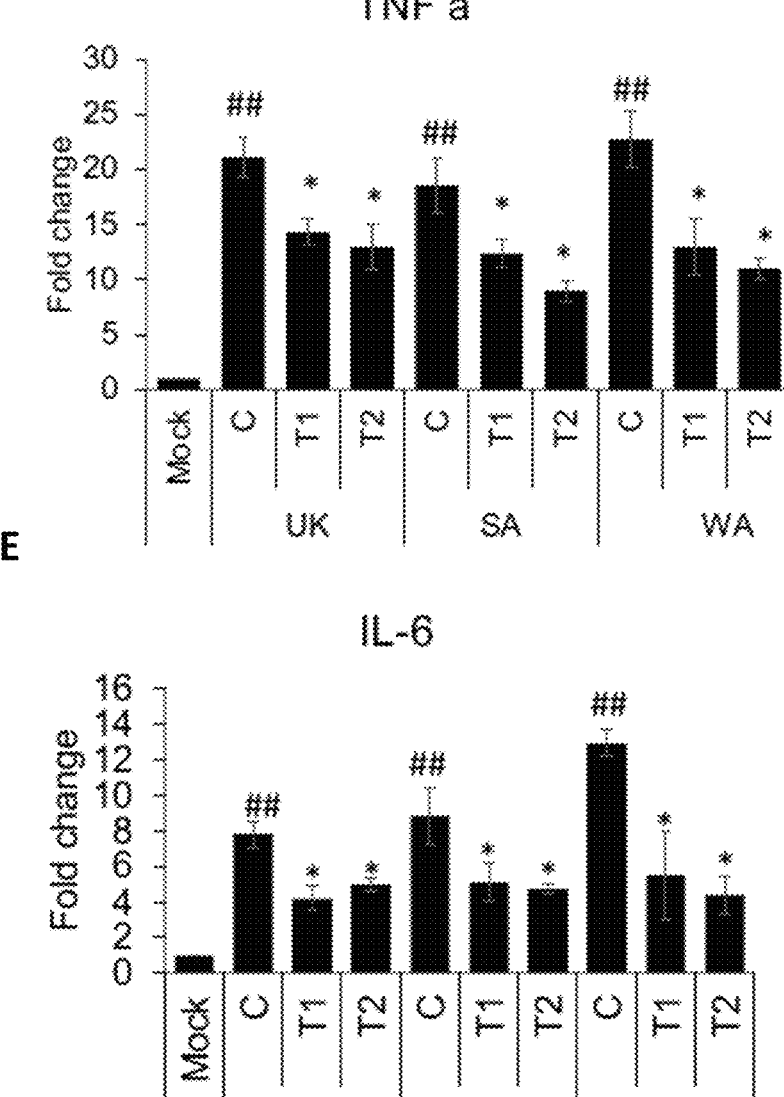
FIG. 4E-F

A
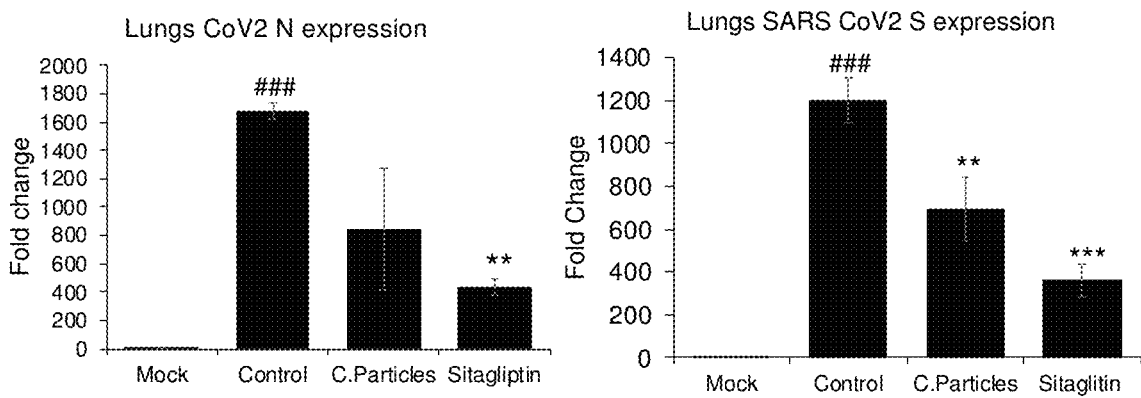
B
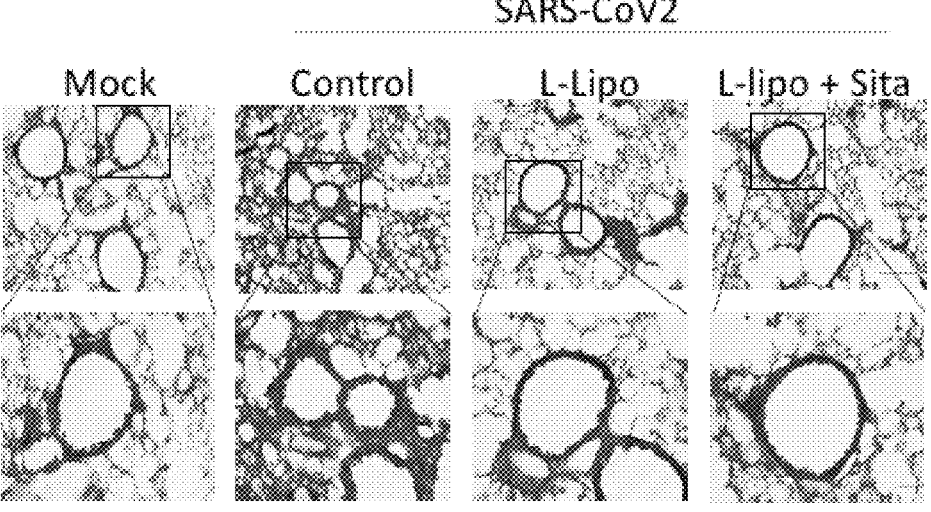
FIG. 6A-B

COMPOSITION AND METHOD FOR TREATING COVID-19

CROSS REFERENCE TO RELATED APPLICATIONS

This application is a continuation of and claims priority to International Patent Application No. PCT/US2022/029366, entitled "Composition and Method for Treating Covid-19", filed May 16, 2022, which is a nonprovisional of and claims priority to U.S. Provisional Patent Application Ser. No. 63/201,819, entitled "Composition and Method of Treating Covid-19 Infection", filed May 14, 2021, and U.S. Provisional Patent Application Ser. No. 63/202,897, entitled "Composition and Method of Treating Covid-19 Infection", filed Jun. 29, 2021, the contents of each of which are hereby incorporated by reference into this disclosure.

GOVERNMENT SUPPORT

This invention was made with Government support under Grant No. BX005490 awarded by the Department of Veterans Affairs. The Government has certain rights in the invention.

FIELD OF INVENTION

This invention relates to treatment and/or prevention of respiratory viruses including coronaviruses. Specifically, the invention provides a method of preventing and/or treating severe acute respiratory syndrome coronavirus 2 (SARS-CoV-2) using a novel single or combination therapeutic agent formulation for obese and/or diabetic patients.

BACKGROUND OF THE INVENTION

The recent emergence of Severe Acute Respiratory Syndrome Virus-2 (SARS-CoV-2, synonym CoV2) in December of 2019 in Wuhan, China, and the subsequent declaration of a pandemic by the World Health Organization, reaffirms the clinical significance of emerging coronaviruses. CoV2 has been characterized as a virus causing pneumonia and severe respiratory distress. These severe manifestations of viral infection, particularly burden both the elderly, adults and young with underlying conditions. [Park SE. Epidemiology, virology, and clinical features of severe acute respiratory syndrome-coronavirus-2 SARS-CoV-2; Coronavirus Disease-19. Clin Exp Pediatr. 2020; 63(4):119-24. Epub Apr. 7, 2020)].

It has been suggested that CoV2 will continue to remain as a serious agent and add to the repertoire of other seasonal respiratory infections caused by influenza, respiratory syncytial virus (RSV), and rhinovirus. Of note, vaccines and a limited number of moderately effective therapies including dexamethasone, remdesivir and molnupiravir are available against CoV2. [McGill A R, Kahlil R, Dutta R, et al. SARS-CoV-2 Immuno-Pathogenesis and Potential for Diverse Vaccines and Therapies: Opportunities and Challenges. Infect Dis Rep. 2021; 13(1):102-25. Epub Feb. 10, 2021]. Monoclonal antibody therapy has also presented some success, however the therapy must be administered within 7 days of the onset of symptoms and is most effective on mild to moderate cases of COVID-19. Unfortunately, however, about one-third of the US population does not practice adequate public health measures such as using face masks or getting vaccinated.

Obesity

Social determinants of health such as access to healthy food, access to healthcare, socioeconomic status, racial and ethnic disparities, location and physical environment, and education are implicated in more severe outcomes from COVID-19 infection. Social determinants of health such as obesity, and its related chronic diseases such as diabetes, hypertension, cardiovascular disease and pulmonary dysfunction, are correlated with severe negative outcomes from COVID-19. [Belanger, M. J. et al., Covid-19 and disparities in nutrition and obesity, *N Engl J Med*, Sep. 10, 2020, 383:11].

It has been suggested that at least 25% of deaths due to COVID-19 occurred in patients that were obese. [Ryan et al., Is adipose tissue a reservoir for viral spread, immune activation, and cytokine amplification in coronavirus disease 2019?, *Obesity*, 2020, 0:1-4]. Obese patients have been found to have a 45% greater risk of death from COVID-19 compared to non-obese patients. [Mahamat-Saleh Y. et al., Diabetes, hypertension, body mass index, smoking and COVID-19 related mortality: a systematic review and meta-analysis of observational studies, *BMJ Open*, 2021 Oct. 25, 11(10):e052777].

Obese patients exist in a state of chronic, low-grade systemic inflammation thus predisposing obese patients to the cytokine storm characteristic of COVID-19. (Belanger 2020). Obesity is known to activate inflammatory cytokines such as tumor necrosis factor alpha (TNFα), interleukin (IL)-1, and IL-6. Obese patients exhibit dysregulated cytokine profiles, endocrine and metabolic derangements, activated renin angiotensin system with depletion and dysfunction of the counterregulatory angiotensin converting enzyme 2 Mas receptor system. Such dysfunction makes adipose tissue, particularly visceral adipose tissue, pro-immunogenic, metabolically active, and highly integrated into the cardiovascular system thus promoting acute disease through augmented inflammation in the heart, vasculature, pancreas, liver, and kidneys. (Ryan 2020).

SARS CoV-2 directly binds with angiotensin-converting enzyme 2 (ACE2) receptors on the cell surface to infect human cells. ACE2 expression is higher in adipose tissue than in lung tissue, thus making adipose tissue vulnerable to COVID-19 infection. (Sanchis-Gomar F. et al., Obesity and outcomes in COVID-19: When an epidemic and pandemic collide, *Mayo Clin Proc*, 2020, 95(7):1445-1453). ACE2 expression is a basis for viral tropism in adipocytes, smooth muscle cells, and endothelial cells in adipose tissue. (Ryan 2020). Adipose tissue may serve as a reservoir for SARS-CoV-2 due to the presence of high levels of angiotensin-converting enzyme 2 (ACE2) thus perpetuating spread of the virus to other organs. (Belanger 2020)

Diabetes

Diabetics are not more likely to become infected with SARS CoV-2, however people with diabetes, particularly Type 2 diabetes, are more likely to develop more severe COVID-19 disease compared to non-diabetics due to increased inflammation or a cytokine storm. People with diabetes inherently have more inflammation in their body and are also prone to having problems with circulation. Patients with diabetes and infected with COVID-19 have a significantly higher inflammatory markers such as C reactive protein (CRP), interleukin 6 (IL-6) compared with patients without diabetes. [Mahamat-Saleh Y. et al., Diabetes, hypertension, body mass index, smoking and COVID-19 related mortality: a systematic review and meta-analysis of observational studies, *BMJ Open*, 2021 Oct. 25, 11(10):e052777].

Diabetes-associated endothelial dysfunction and its related prothombotic state serve to increase the risk of thromboembolic events in diabetic COVID-19 patients. Diabetic endothelial dysfunction and hyperactive inflammatory and immune responses correlated to twofold to threefold higher intensive care hospitalizations and more than twice the mortality among diabetic COVID-19 patients. [Samuel et al., Therapeutic potential of metformin in COVID-19: reasoning for its protective role, *Trends in Microbiology*, October 2021, 29(10):894-907].

Some studies suggest that 30-40% of all COVID-19 deaths in the US occurred in patients diagnosed with diabetes with diabetes accounting for a 14% increase in the absolute risk of death and a 54% higher risk of death from COVID-19 compared to non-diabetics. [Mahamat-Saleh Y. et al., Diabetes, hypertension, body mass index, smoking and COVID-19 related mortality: a systematic review and meta-analysis of observational studies, *BMJ Open,* 2021 Oct. 25, 11(10):e052777]. It has also been found that having COVID-19 seems to raise a person's risk of developing diabetes within the next year by about 40%. The more severe the COVID-19 infection, the higher the risk of developing diabetes.

Long Haul COVID-19

As noted above, inflammation plays a significant role in symptoms experienced by both acute and long haul COVID-19 patients. COVID-19 infection can lead to uncontrolled inflammation, which in turn leads to a cytokine storm, i.e., an exaggerated release of cytokines in response to infection that is due to unregulated release of pro-inflammatory cytokines such as IL-6, IL-1β, and TNFα, among others. COVID-19 infection, caused by the SARS-CoV-2 virus, can cause varying neurological, cardiovascular, respiratory, and inflammatory symptoms in patients. Respiratory symptoms have been well documented and include shortness of breath, difficulty breathing, and cough. Serious lung damage can be caused by COVID-19 infection due to inflammation in the lungs caused by an overexuberant immune response termed the cytokine storm. In addition, inflammation can cause multisystem inflammatory syndrome (MIS) in both adults and children. MIS is a rare, but serious, condition caused by COVID-19 infection in which various body parts become inflamed, such as the heart, lungs, kidneys, brain, skin, eyes, or gastrointestinal organs.

Cardiovascular symptoms such as dizziness, persistent pain or pressure in the chest, tachycardia, and heart palpitations have been reported in COVID-19 patients. In some extreme cases, post-viral heart failure and viral myocarditis have also been reported. Further, hypertension is known to be a comorbidity for COVID-19 infection.

Many patients infected with COVID-19 report having neurological symptoms such as anosmia, ageusia, nausea, impaired consciousness (i.e., "brain fog"), confusion, fatigue, and headache. For some patients, such neurological symptoms may persist for weeks to months after the patient has cleared the virus from their system as discussed below.

In some patients, COVID-19 symptoms may last for weeks or months despite testing negative for the virus. Such patients are termed "long haulers" and have, in theory, recovered from the worst impacts of COVID-19 infection, however, they still exhibit symptoms. These long-haul symptoms can include neurological symptoms, such as brain fog, anosmia, ageusia, insomnia, and headaches. Some long haulers experience symptoms such as debilitating fatigue, body aches, and joint pain. Respiratory symptoms such as coughing, and shortness of breath may also be present as long haul symptoms. Cardiovascular symptoms such as persistent pain or pressure in the chest, tachycardia, dizziness, and heart palpitations have also been reported. [Rubin, R., As their numbers grow, COVID-19 "long haulers" stump experts, *JAMA,* 2020, 324(14):1381-1383].

While it is unknown why long haulers continue to experience symptoms while testing negative for the SARS-CoV-2 virus, alleviation of the symptoms should be considered with any treatment regime. One theory is that the body remains in a heightened immune state after infection, possibly due to small amounts of virus remaining in the body.

Given the lack of available treatments for COVID-19, what is needed is a composition that is efficacious as a treatment and/or preventative for infection by SARS-CoV-2 virus. Specifically, therapeutics that are capable of reducing inflammation and/or neurological, respiratory or cardiovascular symptoms found in long-haulers are needed.

SUMMARY OF INVENTION

The inventors found that singular or combined compositions of therapeutic agents, such as sitagliptin and metformin, optionally integrated in a nanosystem having a targeting moiety, such as linoleic acid, can be used to treat and prevent respiratory virus infection, particularly SARS CoV-2 infection, in patients having comorbidities such as obesity and diabetes, thus decreasing mortality and severity of disease.

In an embodiment, a nanosystem is presented comprising: at least one nanoparticle having at least one targeting moiety to form a targeted nanoparticle wherein the targeting moiety is a fatty acid selected from the group consisting of linoleic acid (LLA), linolenic acid (LNA), oleic acid, and lauric acid and at least one therapeutic agent encapsulated within the at least one targeted nanoparticle wherein the targeting moiety targets a severe acute respiratory syndrome coronavirus 2 (SARS CoV-2) virus.

The at least one therapeutic agent may be selected from peroxisome proliferator activated receptor gamma (PPAR-γ) agonists, dipeptidyl peptidase 4 (DPP4) inhibitors, anti-inflammatory agents, angiotensin converting enzyme (ACE) inhibitors, angiotensin receptor blockers (ARBs), biguanides, and combinations thereof. In some embodiments, the therapeutic agent may be sitagliptin, metformin, or combinations thereof.

In another embodiment, a method of treating a coronavirus infection in a patient in need thereof is presented comprising: administering to the patient in need thereof a therapeutically effective amount of a composition comprising at least one therapeutic agent selected from the group consisting of a dipeptidyl peptidase 4 (DPP4) inhibitor, an anti-inflammatory agent, a PPAR-γ agonist, a biguanide, an angiotensin converting enzyme (ACE) inhibitor, an angiotensin receptor blocker (ARB), and combinations thereof and a pharmaceutically acceptable carrier. After administration of the composition, the patient does not develop severe disease. The coronavirus may be severe acute respiratory syndrome coronavirus 2 (SARS CoV-2) virus. The patient may have one or more comorbidities selected from the group consisting of obesity, diabetes, cardiometabolic syndrome, and visceral fat accumulation.

The composition may be further comprised of at least one nanoparticle having at least one targeting moiety to form a targeted nanoparticle wherein the at least one therapeutic agent is encapsulated within the at least one targeted nanoparticle. The targeting moiety may target the SARS CoV-2 virus and may be a fatty acid selected from the group consisting of linoleic acid (LLA), linolenic acid (LNA), oleic acid, and lauric acid. In some embodiments, the therapeutic agent may be sitagliptin, metformin, or combinations thereof.

In a further embodiment, a method of preventing a coronavirus severe acute respiratory syndrome coronavirus 2 (SARS CoV-2) infection in a patient in need thereof is presented comprising: prophylactically administering to the patient in need thereof a therapeutically effective amount of a composition comprising at least one therapeutic agent selected from the group consisting of a dipeptidyl peptidase 4 (DPP4) inhibitor, an anti-inflammatory agent, a PPAR-γ agonist, a biguanide, an angiotensin converting enzyme (ACE) inhibitor, an angiotensin receptor blocker (ARB), and combinations thereof and a pharmaceutically acceptable carrier wherein the prophylactic administration of the composition to the patient in need thereof inhibits the coronavirus infection. The coronavirus may be severe acute respiratory syndrome coronavirus 2 (SARS CoV-2) virus. The patient may have one or more comorbidities selected from the group consisting of obesity, diabetes, cardiometabolic syndrome, and visceral fat accumulation.

The composition may be further comprised of at least one nanoparticle having at least one targeting moiety to form a targeted nanoparticle wherein the at least one therapeutic agent is encapsulated within the at least one targeted nanoparticle. The targeting moiety may target the SARS CoV-2 virus and may be a fatty acid selected from the group consisting of linoleic acid (LLA), linolenic acid (LNA), oleic acid, and lauric acid. In some embodiments, the therapeutic agent may be sitagliptin, metformin, or combinations thereof.

BRIEF DESCRIPTION OF THE DRAWINGS

For a fuller understanding of the invention, reference should be made to the following detailed description, taken in connection with the accompanying drawings, in which:

FIG. 1A-B are a series of images depicting (A) the receptor binding domain (RBD)/ACE2 for sitagliptin; and (B) the RBD/DPP4 for sitagliptin.

FIG. 2A-D are a series of images depicting the effects of metformin and sitagliptin on SARS CoV-2 infected Caco2 cells. (A) CoV-2-GFP infected (2 MOI) Caco2 cells were visualized by fluroscent microscopy after treatment with metformin (10 mM) or sitagliptin (20 uM); (B) graph of fold change of SARS CoV-2 N protein after treatment with metformin or sitagliptin; (C) graph of fold change of SARS CoV-2 S protein after treatment with metformin or sitagliptin; (D) graph of fold change of IL-6, IL-1β, and TNFα after treatment with metformin or sitagliptin. Data expressed as mean±SEM, Mock—UV inactivated, * compared to control, # Compared to blank (Mock); *p<0.05, p<0.005, ####, *p<0.0005.

FIG. 3A-B are a series of images depicting the effects of therapeutic agents on SARS CoV-2 infection in mature adipocytes. (A) staining of GFP-CoV-2 infected (2 MOI) cells after treatment with metformin (10 mM) or sitagliptin (20 uM). (B) graph showing integrated density of GFP expression after treatment with metformin or sitagliptin. Data expressed as mean±SEM, * compared to control; *p<0.05, p<0.005, ####,*p<0.0005

6 sitagliptin. Data expressed as mean±SEM, * compared to control; *p<0.05, p<0.005, ####,*p<0.0005

FIG. 4A-D are a series of images depicting the effects of sitagliptin (20 uM) or sitagliptin monohydrate phosphate (20 uM) on SARS CoV-2 (variants) infected Calu3 cells, (WA-GFP, Washington strain with GFP, UK, United Kingdom B.1.1.7, SA, South Africa B.1.351). (A) cell staining for Washington strain with GFP; (B) cell staining for South African B.1.351 variant; (C) cell staining for United Kingdom B.1.1.7 variant; (D) histogram showing mRNA expression level of SARS CoV-2 N protein assessed by qPCR, from RNA samples isolated from Calu3 cells infected with SARS CoV2. Data expressed as mean±SEM, # Compared to blank (Mock), * Compared to control #,*p<0.05, ###,p<0.005, ####,*p<0.0005.

FIG. 4E-F are a series of images depicting the effects of sitagliptin (20 uM) and sitagliptin monohydrate phosphate (20 uM) on SARS CoV-2 (variants) infected Calu3 cells, (WA-GFP, Washington strain with GFP, UK, United Kingdom B.1.1.7, SA, South Africa B.1.351). (E) histogram showing mRNA expression level of inflammatory gene TNFα assessed by qPCR, from RNA samples isolated from Calu3 cells infected with SARS CoV2; (F) histogram showing mRNA expression level of inflammatory gene IL-6 assessed by qPCR, from RNA samples isolated from Calu3 cells infected with SARS CoV2. Data expressed as mean±SEM, # Compared to blank (Mock), * Compared to control #; *p<0.05, ###,p<0.005, ####,*p<0.0005.

Figure 5:
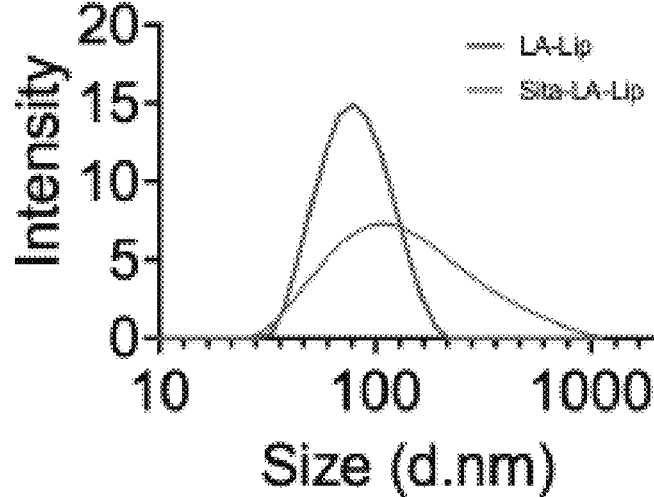

FIG. 5 is an image depicting the synthesis of Sitagliptin-loaded Linoleic acid liposomal Nanoparticles. Sitagliptin-loaded liposomes, with encapsulated Linoleic acid on the lipid bilayer were prepared using thin-film hydration method. Briefly, hydrogenated L-α phosphatidylcholine (PC), cholesterol and Linoleic Acid (LA) at a ratio of 6:1:3 (wt/wt) were dissolved in methanol: chloroform mixture (1:2 v/v). The solvent was removed using rotary evaporation. To completely remove the organic solvents a stream of argon was applied for 10 minutes. The thin film was hydrated with 50 mg/ml Sitagliptin phosphate monohydrate solution in dH20 (adjusted at 300 mOsm with NaCl, pH 7.4) at 40° C. The size of the particles was reduced using probe sonication until they became clear and centrifuged (12,000 rpm, 10 min) in order to precipitate and discard large liposome aggregates and titanium particles that leaked from the probe. Finally, liposome dispersions were incubated for 1 h at 40° C. in order to anneal structural defects. After annealing, the nonencapsulated Sitagliptin was separated by Size Exclusion Chromatography (Sephadex G-50 fine column). To determine the sitagliptin-lipid ratio of the liposomal formulation, sitagliptin was extracted in Chloroform: Water (1:1 v/v) biphasic system. The amount of sitagliptin in the aqueous phase (encapsulated sitagliptin) was determined by UV absorption at 270 nm. The lipid concentration was estimated using Stewart assay. The final ratio for PC: was found to be PC:Sitagliptin 63:25 (wt/wt). Particle size was measured by dynamic light scattering (DLS, Malvern Nano-Z) at 25° C. at a 173° angle.

FIG. 6A-B are a series of images depicting the effect of linoleic liposomal nanoparticles and sitagliptin in SARS CoV-2 infected mice. The mice were intranasally infected with SARS CoV2 (100 k PFU), on Day 0 and treated with PBS (control), Linoleic acid liposomes (L-lipo), and liposome encapsulating sitagliptin (L-lipo+sita)-25 ug/1 mg/kg for 5 days and sacrificed on day 7. (A) Histograms showing mRNA expression level of SARS CoV 2 N protein, S Protein, assessed by qPCR, from RNA samples isolated from lung and brain samples from CoV2 infected hACE2 mice and samples were collected 7 days post infection, Mock—UV inactivated virus, Data expressed as mean±SEM, n=3, * Compared to Mock, # Compared to Mock *p<0.05,p<0.005, ###,*p<0.0005. (B) The tissues were cryosectioned and Periodic acid-Schiff staining was performed, scale bar—Top panel 100 u, bottom panel 20 u.

DETAILED DESCRIPTION OF THE PREFERRED EMBODIMENT

In the following detailed description of the preferred embodiments, reference is made to the accompanying drawings, which form a part hereof, and within which are shown by way of illustration specific embodiments by which the invention may be practiced. It is to be understood that other embodiments may be utilized, and structural changes may be made without departing from the scope of the invention.

Definitions

Unless otherwise defined, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are described herein. All publications mentioned herein are incorporated herein by reference in their entirety to disclose and describe the methods and/or materials in connection with which the publications are cited. It is understood that the present disclosure supercedes any disclosure of an incorporated publication to the extent there is a contradiction.

As used herein, the singular forms "a," "an" and "the" include plural referents unless the context clearly dictates otherwise. For example, "a nanoparticle" includes "nanoparticles" or "plurality of nanoparticles".

As used in this specification and the appended claims, the term "or" is generally employed in its sense including "and/or" unless the context clearly dictates otherwise.

All numerical designations, such as pH, temperature, time, concentration, and molecular weight, including ranges, are approximations which are varied up or down by increments of 1.0, 0.1, 0.01 or 0.001 as appropriate. It is to be understood, even if it is not always explicitly stated that all numerical designations are preceded by the term "about". It is also to be understood, even if it is not always explicitly stated, that the reagents described herein are merely exemplary and that equivalents of such are known in the art and can be substituted for the reagents explicitly stated herein.

As used herein, the term "comprising" is intended to mean that the products, compositions, and methods include the referenced components or steps, but not excluding others. "Consisting essentially of" when used to define products, compositions, and methods, shall mean excluding other components or steps of any essential significance. Thus, a composition consisting essentially of the recited components would not exclude trace contaminants and pharmaceutically acceptable carriers. "Consisting of" shall mean excluding more than trace elements of other components or steps.

As used herein, "about" means approximately or nearly and in the context of a numerical value or range set forth means±15% of the numerical.

As used herein "patient" is used to describe a mammal, preferably a human, to whom treatment is administered, including prophylactic treatment with the compositions of the present invention. "Patient" and "subject" are used interchangeably herein.

As used herein "animal" means a multicellular, eukaryotic organism classified in the kingdom Animalia or Metazoa. The term includes, but is not limited to, mammals. Non-limiting examples of mammals include humans, rodents, aquatic mammals, domestic animals such as dogs and cats, farm animals such as sheep, pigs, cows and horses. Wherein the terms "animal" or the plural "animals" are used, it is contemplated that it also applies to any animals.

"Administering" or "administration" as used herein refers to the process by which the compositions of the present invention are delivered to the patient. The compositions may be administered in various ways, including but not limited to, orally, nasally, and parenterally.

A "therapeutic agent" as used herein refers to a substance, component or agent that has measurable specified or selective physiological activity when administered to an individual in a therapeutically effective amount. Examples of therapeutic agents as used in the present invention include anti-inflammatory agents and/or antivirals, such as PPARγ agonists leriglitazone, pioglitazone and other metabolites of pioglitazone; angiotensin converting enzyme (ACE) inhibitors such as captopril, benazepril, fosinopril, lisinopril, moexipril, perindopril, quinapril, and enalapril; angiotensin receptors blockers (ARBs) such as azilsartan, candesartan, eprosartan, irbesartan, losartan, olmesartan, telmisartan, and valsartan; dipeptidyl peptidase 4 (DPP4) inhibitors such as sitagliptin, saxagliptin, linagliptin, and alogliptin; dual DPP4 and ACE2 inhibitors such as sitagliptin and leriglitazone; and biguanides such as metformin. At least one therapeutic agent is used in the compositions of the present invention, however in some embodiments, multiple therapeutic agents are used. In some embodiments, one or more therapeutic agents may be encapsulated within a nanoparticle. In some embodiments, a targeted nanoparticle may act on its own as a therapeutic agent without another drug being encapsulated within. The targeting moiety in such targeted nanoparticle may be a fatty acid such as linoleic acid (LLA), linolenic acid (LNA), oleic acid, or lauric acid.

A "therapeutically effective amount" as used herein is defined as concentrations or amounts of components which are sufficient to effect beneficial or desired clinical results, including, but not limited to, any one or more of treating symptoms of coronaviruses, particularly CoV-2 infection and preventing coronavirus infection, particularly CoV-2 infection. Compositions of the present invention can be used to effect a favorable change in the condition whether that change is an improvement, such as stopping, reversing, or reducing CoV-2 infection, or a complete elimination of symptoms due to CoV-2 infection. In accordance with the present invention, a suitable single dose size is a dose that is capable of preventing or alleviating (reducing or eliminating) a symptom in a patient when administered one or more times over a suitable time period. One of skill in the art can readily determine appropriate single dose sizes for systemic administration based on the size of the animal and the route of administration. The dose may be adjusted according to response.

The amount of the compound in the drug composition will depend on absorption, distribution, metabolism, and excretion rates of the drug as well as other factors known to those of skill in the art. Dosage values may also vary with the severity of the condition to be alleviated. The compounds may be administered once, or may be divided and administered over intervals of time. It is to be understood that administration may be adjusted according to individual need and professional judgment of a person administrating or supervising the administration of the compounds used in the present invention.

The dose of the compounds administered to a subject may vary with the particular composition, the method of administration, and the particular disorder being treated. The dose should be sufficient to affect a desirable response, such as a therapeutic or prophylactic response against a particular disorder or condition. It is contemplated that one of ordinary skill in the art can determine and administer the appropriate dosage of compounds disclosed in the current invention according to the foregoing considerations.

Dosing frequency for the composition includes, but is not limited to, at least about once every three weeks, once every two weeks, once a week, twice a week, three times a week, four times a week, five times a week, six times a week, or daily. In some embodiments, the interval between each administration is less than about a week, such as less than about any of 6, 5, 4, 3, 2, or 1 day. In some embodiments, the interval between each administration is constant. For example, the administration can be carried out daily, every two days, every three days, every four days, every five days, or weekly. In some embodiments, the administration can be carried out twice daily, three times daily, or more frequent. Administration can also be continuous and adjusted to maintaining a level of the compound within any desired and specified range.

The administration of the composition can be extended over an extended period of time, such as from about a month or shorter up to about three years or longer. For example, the dosing regimen can be extended over a period of any of about 2, 3, 4, 5, 6, 7, 8, 9, 10, 11, 12, 18, 24, 30, and 36 months. In some embodiments, there is no break in the dosing schedule. In some embodiments, the interval between each administration is no more than about a week.

The compounds used in the present invention may be administered individually, or in combination with or concurrently with one or more other compounds used against viruses, including coronaviruses such as SARS CoV-2. Additionally, compounds used in the present invention may be administered in combination with or concurrently with other therapeutics for coronaviruses or other respiratory viruses.

"Prevention" or "preventing" or "prophylactic treatment" as used herein refers to any of: halting the effects of coronavirus infection, reducing the effects of coronavirus infection, reducing the incidence of coronavirus infection, reducing the development of coronavirus infection, delaying the onset of symptoms of coronavirus infection, increasing the time to onset of symptoms of coronavirus infection, and reducing the risk of development of coronavirus infection. In some embodiments, the coronavirus infection is SARS CoV-2.

"Treatment" or "treating" as used herein refers to any of the alleviation, amelioration, elimination and/or stabilization of a symptom, as well as delay in progression of a symptom of a particular disorder. For example, "treatment" of coronavirus infection may include any one or more of the following: amelioration and/or elimination of one or more symptoms associated with coronavirus infection, reduction of one or more symptoms of coronavirus infection, stabilization of symptoms of coronavirus infection, and delay in progression of one or more symptoms of coronavirus infection. Treatment may include reduction of viral replication in cells and/or reducing inflammation associated with coronavirus infection as shown through reduction in inflammatory cytokine expression. In some embodiments, the coronavirus infection is CoV-2.

"Infection" as used herein refers to the invasion of one or more microorganisms such as bacteria, viruses, fungi, yeast, or parasites in the body of a patient in which they are not normally present. In certain embodiments, the infection is from a respiratory virus such as a respiratory syncytial virus, Influenza virus, or coronavirus. In some embodiments, the coronavirus is severe acute respiratory syndrome coronavirus 2 (SARS-CoV-2). Other coronaviruses contemplated herein include, but are not limited to, severe acute respiratory syndrome coronavirus 1 (SARS-CoV-1), Middle East respiratory syndrome coronavirus (MERS-CoV), human coronavirus OC43 (HcoV-OC43), human coronavirus 229E (HcoV-229E), porcine deltacoronavirus (PDCoV) (porcine), infectious bronchitis virus (IBV, avian), and other coronaviruses of pandemic potential including Delta coronavirus, duvinacovirus, Embecovirus, Gammacoronavirus, Merbecovirus, Nobecovirus and Sarbecovirus.

The pharmaceutical compositions of the subject invention can be formulated according to known methods for preparing pharmaceutically useful compositions. Furthermore, as used herein, the phrase "pharmaceutically acceptable carrier" means any of the standard pharmaceutically acceptable carriers. The pharmaceutically acceptable carrier can include diluents, adjuvants, and vehicles, as well as implant carriers, and inert, non-toxic solid or liquid fillers, diluents, or encapsulating material that does not react with the active ingredients of the invention. Examples include, but are not limited to, phosphate buffered saline, physiological saline, water, and emulsions, such as oil/water emulsions. The carrier can be a solvent or dispersing medium containing, for example, ethanol, polyol (for example, glycerol, propylene glycol, liquid polyethylene glycol, and the like), suitable mixtures thereof, and vegetable oils. Formulations are described in a number of sources that are well known and readily available to those skilled in the art. For example, *Remington's Pharmaceutical Sciences* (Martin E W [1995] Easton Pennsylvania, Mack Publishing Company, 19th ed.) describes formulations which can be used in connection with the subject invention.

For ease of administration, the subject compounds may be formulated into various pharmaceutical forms. As appropriate compositions there may be cited all compositions usually employed for systemically or topically administering drugs. To prepare the pharmaceutical compositions of this invention, atranorin or other polyphenolic lichen acid isolate, as the active ingredient is combined in intimate admixture with a pharmaceutically acceptable carrier, which may take a wide variety of forms depending on the form of preparation desired for administration. These pharmaceutical compositions are desirably in unitary dosage form suitable, preferably, for administration nasally, orally, rectally, percutaneously, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules often represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution.

"Nanoparticle" as used herein refers to a particle or structure which is biocompatible with and sufficiently resistant to chemical and/or physical destruction by the environment of such use so that a sufficient number of the nanoparticles remain substantially intact after delivery to the site of application or treatment and whose size is in the nanometer range. For the purposes of the present invention, a nanoparticle typically ranges between about 1 nm to about 1000 nm, preferably between about 50 nm and about 500 nm, more preferably between about 50 nm and about 350 nm, more preferably between about 100 nm and about 250 nm. As used herein, the term "nanoparticle" includes, but is not limited to, micelles, polymeric nanoparticles, and lipid-based nanoparticles such as liposomes and niosomes.

"Polymer" as used herein refers to a relatively high molecular weight organic compound, natural or synthetic, whose structure can be represented by a repeated small unit, the monomer. Synthetic polymers are typically formed by addition or condensation polymerization of monomers. A polymer comprised of two or more different monomers is a copolymer. In some embodiments, the polymers used to form the nanoparticles include, but are not limited to, L-α phosphatidylcholine (PC), poly(lactic acid-co-glycolic acid) (PLGA), poly(vinyl alcohol) (PVA), and polyacrylic acid.

"Targeting moiety" as used herein refers to a fatty acid, peptide, aptamer, antibody, protein, carbohydrate, vitamin, or organic small molecule capable of being linked to a nanoparticle and having an affinity for a specific binding partner on a coronavirus viral particle. The targeting ligand is preferably selective as opposed to non-selective. In some embodiments where the coronavirus is SARS CoV-2, the targeting moiety binds to the CoV-2 spike protein or ACE2-spike interface. In some embodiments, the at least one targeting moiety is used and is a fatty acid including, but not limited to, linoleic acid (LLA), linolenic acid (LNA), oleic acid, and lauric acid. In some embodiments, the targeting moiety is encapsulated in the lipid bilayer of the nanoparticle. In some embodiments, the nanoparticle itself, in conjunction with the targeting moiety, acts as the therapeutic agent in the absence of a drug also being encapsulated within the nanoparticle.

"Therapeutic nanoparticle" as used herein refers to nanoparticles containing at least one therapeutic agent. In some embodiments, the therapeutic nanoparticles contain a PPARγ agonist, a DPP4 inhibitor, an ACE inhibitor, an ARB, a biguanide, an anti-inflammatory agent, or a combination thereof. In some embodiments, the therapeutic nanoparticles have a targeting moiety attached.

"Targeting nanoparticles" or "targeting nanoparticle composition" as used herein refers to at least one therapeutic nanoparticle, optionally suspended in a pharmaceutically acceptable carrier. In some embodiments, the targeting nanoparticles of the instant invention are used to treat coronavirus infections. In some embodiments, the coronavirus infection is a SARS CoV-2 infection.

COVID may continue as a seasonal endemic or may return as an epidemic in the future. COVID and other viral infections can lead to higher blood sugar levels and increase the risk of short term complications such as ketoacidosis and a hyperosmolar hyperglycemic state. There is a dire need to develop therapies that intervene COVID infection in the lungs and adipocytes to provide health benefits to diabetic and obese patients.

Obesity, Diabetes, and COVID-19

Obesity is a known risk factor for cardiovascular disease, Type II diabetes, metabolic syndrome, hypertension, chronic lung disease, asthma, and systemic inflammation. Obesity also has adverse effects on cardiovascular structure and function.

SARS CoV-2 directly binds to ACE2 receptors on the cell surface to enter cells. ACE2 expression is higher in adipose tissue than in lung tissue which suggests that adipose tissue may be more vulnerable to COVID-19 infection which may lead to adipose tissue being a viral reservoir for SARS CoV-2. Obese people have more adipose tissue and thus higher ACE2 levels. Some studies have proposed that obese patients having COVID-19 infection had elevated Angiotensin II levels that correlated with severity of lung injury. High angiotensin II levels in the lung can lead to pulmonary vasoconstriction which may in turn lead to ventilation/perfusion mismatch, hypoxemia, inflammation, and oxidative damage thus promoting acute lung injury. Angiotensin II levels have been shown to correlate with body weight which may exacerbate COVID-19-induced Angiotensin II level increase thus leading to more severe lung injury. (Sanchis-Gomar F. et al., Obesity and outcomes in COVID-19: When an epidemic and pandemic collide, *Mayo Clin Proc*, 2020, 95(7):1445-1453).

Factors contributing to obesity include societal, nutritional, and genetic factors as well as amount of physical activity. Obesity contributes to several comorbidities including, but not limited to, insulin resistance, cardiometabolic syndrome, non-alcoholic fatty liver disease, visceral fat accumulation, and Type 2 diabetes. An obese person has more adipose tissue thus allowing more virus to be present in a viral reservoir in adipose tissue. Increased adipose tissue also increases cytokine production and release as well as immune cell activation. These increases in conjunction with any comorbidities, can result in organ/tissue dysfunction such as dysfunction in the brain, heart, kidneys, gastrointestinal tract, peripheral nerves, skin, endothelial dysfunction, microcirculatory dysfunction, coagulopathy, or hypoperfusion. According to Virchow's Triad, damage to the vascular wall, stasis/impaired flow, and hypercoagulation are exacerbated by obesity and associated metabolic abnormalities.

ACE2 Expression in Adipocytes

Angiotensin converting enzyme (ACE) cleaves angiotensin-I to generate angiotensin-II. acts via the angiotensin type-1 (AT-1) receptor (the target for angiotensin receptor blockers—ARBs), to promote pressor, pro-inflammatory, profibrotic, and pro-thrombotic activity. Simultaneously, but in contrast, the ACE2 (the gateway for SARS-Cov-2 entry into cells) pathway of the renin-angiotensin system (RAS), counteracts the ACE pathway by cleaving angiotensin-II to angiotensin 1-7, thereby reducing angiotensin-II availability to the AT-1 receptor. Angiotensin 1-7, acts via the MAS-receptor, to induce vasodepressor, anti-inflammatory, anti-oxidative, and antiproliferative actions. The binding of the SARS CoV-2 spike protein to ACE2 disturbs the balance between the ACE and ACE2 pathways by downregulating ACE2. This downregulation diminishes the protective effects of the ACE2 pathway with regard to acute inflammation while simultaneously releasing pro-inflammatory and pro-thrombotic activity. [Bryan Williams, Renin angiotensin system inhibition as treatment for Covid-19?, *EClinicalMedicine*, 2021, 37:101023].

As noted previously, an obese patient is particularly vulnerable to severe disease and complications from SARS CoV-2 infection. Comorbidities associated with obesity such as Type 2 diabetes, renal insufficiency, endothelial dysfunction, and cardiovascular diseases, are major risk factors for disease severity and mortality associated with COVID-19. Obesity is also associated with production and release of pro-inflammatory cytokines which lead to chronic inflammation. Obesity also disturbs immune system integrity and significantly alters leukocyte growth, movement and diversity thus resulting in a change in overall immune defense. Obesity also contributes to leptin resistance which impairs immune function. Obesity is also associated with coagulopathy and thrombosis which may also lead to increased mortality among obese patients infected with COVID-19. [Mohammad S., et al., Obesity and COVID-19: what makes obese host so vulnerable?, *Immunity & Ageing*, 2021, 18:1].

Increased production of angiotensinogen by adipose tissue leads to elevated angiotensin (Ang) II levels in obesity. SARS-CoV-2 attenuates Ang II metabolism by binding to angiotensin-converting enzyme 2 (ACE2), promoting a system imbalance. High Ang II levels lead to pulmonary vasoconstriction and inflammation that contributes to acute lung injury (left). ACE2 expression in adipose tissue is higher than that in the lung, a major target organ affected by coronavirus disease 2019 (COVID-19). Increased ACE2 expression in adipocytes may make them more vulnerable to SARS-CoV-2 infection and a potential viral reservoir leading to prolonged viral clearance (middle). AT1R=angiotensin II type I receptor; MasR=G-protein coupled Mas receptor. Dysregulated fatty acid metabolism, cellular hypertrophy and death, ER stress, Hypoxia and mitochondrial dysfunction, because of excess fat leads to a substantial alteration of cellular architecture of adipose tissue (right). This rearrangement favors a pro-inflammatory environment and perpetuates local as well as systemic inflammation. [Sanchis-Gomar 2020; Mohammad 2021]

DPP4 Inhibitors

Dipeptidyl peptidase-4 (DPP4) has been shown to interact with several proteins important for viral processes and immune responses, including ACE2. DPP4 may represent a co-receptor for SARS CoV-2 entry into cells as it displays analogous expression patterns with ACE2 in several human tissues. [Bardaweel et al., Sitagliptin: a potential drug for the treatment of COVID-19?, *Acta Pharm.*, 2021, 71:175-184]. As such, DPP4 represents a novel target in the treatment, including prophylactic treatment, of SARS CoV-2 infection.

SARS CoV-2 spike receptor-binding domain has a potentially high affinity to DPP4 with SARS CoV-2/DPP4 binding sharing key DPP4 residues with that of MERS CoV-S/DPP4. E484 and adjacent mutations are critical for the DPP4-binding ability of SARS CoV-2-S. [(Li 2020)]. SARS-CoV-2 spike protein shares a 31.9% sequence identity with the spike protein present in MERS-CoV. [(Bardaweel 2021)].

DPP4 inhibitors useful in the instant invention include, but are not limited to, sitagliptin, saxagliptin, linagliptin, alogliptin, and combinations thereof. Sitagliptin is known for its antidiabetic, immunoregulatory, anti-inflammatory, anti-apoptotic, and beneficial cardiometabolic effects. [(Bardaweel 2021)]. Administration of sitagliptin to Type 2 diabetic patients has significantly decreased serum levels of inflammatory markers and increased anti-inflammatory cytokines. [Dastan et al., Sitagliptin repositioning in SAARS-CoV-2: effects on ACE-2, CD-26, and inflammatory cytokine storms in the lung, *Iran J Allergy Asthma Immunol, May* 2020, 19 (Suppl. 1):10-12]. It has also been shown to suppress the production of interferon gamma-induced protein 10 (CXCL10) chemokine in AIDS patients. High expression levels of CXCL10 chemokine has been detected in the lung bronchoalveolar microenvironment of COVID-19 patients. Sitagliptin has also been shown to inhibit ACE activity and reduce angiotensin II levels. [(Bardaweel 2021)].

Since ACE2 and DPP4 are critical receptors expressed by many cells and tissues, therapeutic agents which target both receptors to inhibit or downregulate them are an attractive option for treatment and prophylaxis. Examples of such therapeutic agents include sitagliptin. As shown in FIG. 4, sitagliptin is capable of binding to ACE2 and DPP4.

PPARγ Agonists

Discovery of a broad anti-viral and -inflammatory activity has provided a new impetus for novel coronavirus therapy. The CoV-2 pandemic has inspired a molecular docking analysis of FDA approved drugs that bind to the CoV2 Spike protein. The inventors previously found that pioglitazone (PG) had one of the top docking scores. Pioglitazone is a PPAR-γ agonist which has previously been found to inhibit secretion of pro-inflammatory cytokines and increase secretion of anti-inflammatory cytokines. [Qiu D, Li X N. Pioglitazone inhibits the secretion of proinflammatory cytokines and chemokines in astrocytes stimulated with lipopolysaccharide. Int J Clin Pharmacol Ther 2015 September; 53(9):746-52]. Specifically, pioglitazone was found to significantly reduce IL-6 and TNFα mRNA expression to attenuate lung injury. [Kutsukake M, Matsutani T, Tamura K, et al. Pioglitazone attenuates lung injury by modulating adipose inflammation. J Surg Res. 2014; 189(2):295-303].

Leriglitazone (LG) is a soluble orally bioavailable metabolite of PG, which was previously reported to possess potent antiviral activity, particularly against certain RNA viruses such as respiratory syncytial virus (RSV). [Mayilsamy K, Markoutsa E, Das M, et al. Treatment with shCCL20-CCR6 nanodendriplexes and human mesenchymal stem cell therapy improves pathology in mice with repeated traumatic brain injury. Nanomedicine: nanotechnology, biology, and medicine. 2020; 29:102247. Epub Jan. 7, 2020; Matthews L, Kleiner D E, Chairez C, et al. Pioglitazone for Hepatic Steatosis in HIV/Hepatitis C Virus Coinfection. AIDS Res Hum Retroviruses. 2015; 31(10): 961-6. Epub Jul. 28, 2015; Das M, Wang C, Bedi R, et al. Magnetic micelles for DNA delivery to rat brains after mild traumatic brain injury. Nanomedicine: nanotechnology, biology, and medicine. 2014; 10(7):1539-48. Epub Feb. 4, 2014; Wan C J, Dong L, Lin J, et al., [PPARgamma agonists against respiratory syncytial virus infection in vitro study]. Zhonghua Shi Yan He Lin Chuang Bing Du Xue Za Zhi. 2011; 25(6):480-2; Arnold R, Konig W. Peroxisome-proliferator-activated receptor-gamma agonists inhibit the release of proinflammatory cytokines from RSV-infected epithelial cells. Virology. 2006; 346(2):427-39. Epub Dec. 7, 2005)].

Leriglitazone has been found to significantly reduce biomarkers related to inflammation such as matrix metalloproteinase 9, interleukin-18, interleukin-1β, interleukin-1 receptor agonist, and macrophage inflammatory protein 1β. It is a selective peroxisome proliferator-activated receptor γ agonist (PPAR-γ agonist) that is thought to protect neurons and astrocytes by preventing monocyte and microglial activation. Administration of a therapeutically effective amount of leriglitazone can decrease inflammation by reducing the cytokine storm. This decrease in proinflammatory cytokines aids in an anti-inflammatory response that can resolve inflammatory symptoms associated with CoV-2 infection in the respiratory system, as well as symptoms of other body systems, such as joint pain, body aches, and fatigue. LG is capable of inhibiting infection through inhibition of the spike-ACE2 interaction.

The inventors find that a combination of an anti-inflammatory agent, such as the dual ACE2/DPP4 inhibitor sitagliptin, encapsulated in a nanoparticle having a targeting moiety such as linoleic acid (LLA) is able to both treat and prevent CoV-2 infection. Such combination treatment is advantageous in that the therapeutic agents synergistically act together to reduce multiple neurological and inflammatory symptoms caused by CoV-2 infection as well as prevent long COVID.

The following non-limiting examples illustrate exemplary systems and components thereof in accordance with various embodiments of the disclosure. The examples are merely illustrative and are not intended to limit the disclosure in any way.

Example 1—Molecular Modeling of the Receptor Binding Domain (RBD)/ACE2 and RBD/DPP4 for Sitagliptin As shown in FIG. 1A-B, the molecular modeling of the RBD/ACE2 and RBD/DPP4 for sitagliptin suggests potential inhibition of CoV2 infection.

Example 2—Effects of Metformin and Sitagliptin on SARS CoV-2 Infected Caco2 Cells As shown in FIG. 2, both metformin and sitagliptin were capable of decreasing expression of SARS CoV-2 N and S proteins in infected Caco2 cells, with sitagliptin exhibiting a larger decrease than metformin. Further, both metformin and sitagliptin were capable of decreasing expression of IL-6, IL-1β, and TNFα.

Figure 3C:
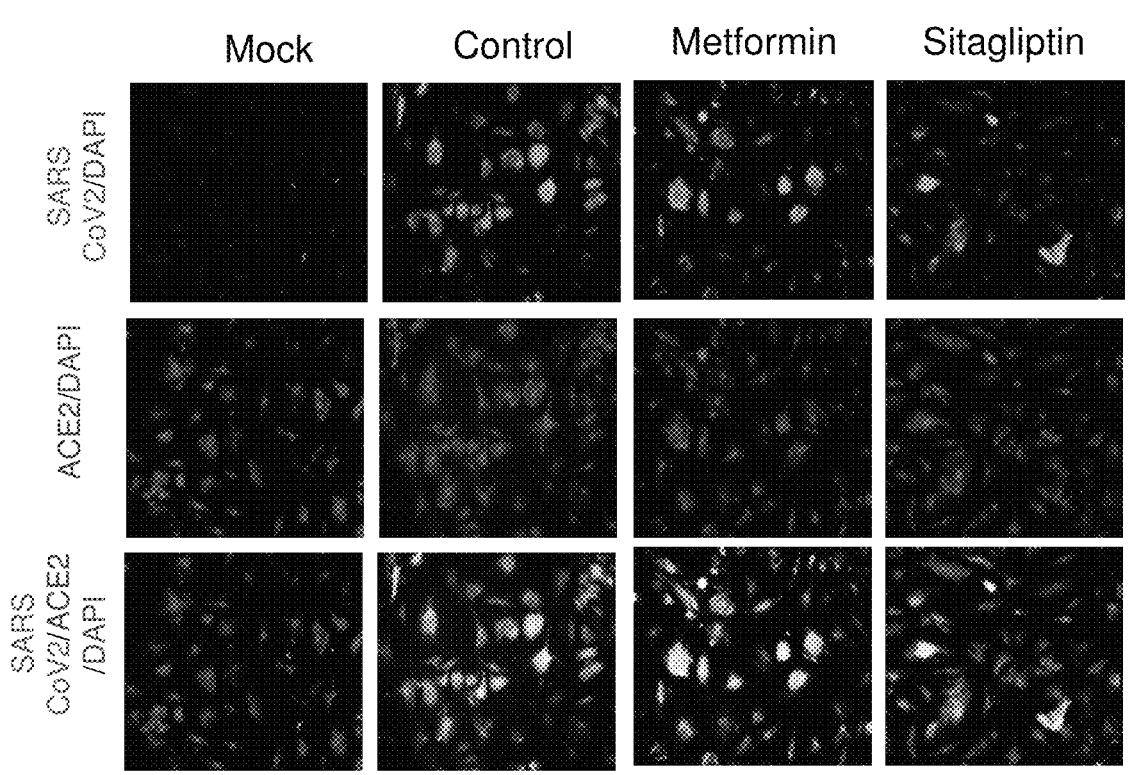
FIG. 3C is an image depicting staining of cells infected with SARS CoV-2 after treatment with metformin or sitagliptin, ACE2 receptor binding after treatment with metformin or sitagliptin, and merged SARS CoV-2 infection/ACE2 receptor binding after treatment with metformin.

Example 3—SARS CoV-2 Infection in Mature Adipocytes: Effects of Therapeutic Agents Adipocytes form a major tissue for the expansion of the SARS-CoV-2 virus. Therefore, adipocytes were infected with SARS-CoV-2 to test effect of various drugs including metformin and sitagliptin. The results showed that each of the drugs tested inhibited viral infection and the magnitude of inhibition varied with highest reduction seen in sitagliptin followed by metformin (FIG. 3A-B). Also, analysis of cytoimmunochemical staining of cells treated with these different drugs showed that each of the drugs showed reduction in infection with sitagliptin showing highest reduction. (FIG. 3C)

Example 4—SARS CoV-2 Variants Infection in Calu3 Cells: Effects of Sitagliptin and Sitagliptin Monohydrate Phosphate FIGS. 4A-F display effects of sitagliptin or sitagliptin monohydrate phosphate in Calu3 cells infected with SARS CoV2 variants. Calu 3 cells infected with SARS CoV2 (WA-GFP, Washington strain with GFP, UK, United Kingdom B.1.1.7, SA, South Africa B.1.351). Cells were imaged 48 hrs of post infection with CoV2 virus (0.1 MOI). Histograms showing mRNA expression level of SARS CoV2 N protein and inflammatory genes (TNFα, IL-6) assessed by qPCR, from RNA samples isolated from infected Calu 3 cells. Cells were collected 48 hrs of post infection with CoV2 virus (0.1 MOI) (C, Control-only infection) and T1, treatment with sitagliptin (in DMSO-20 uM), T2, treatment with sitagliptin monohydrate phosphate (in water 20 uM), n=3, Data expressed as mean±SEM, # Compared to blank (Mock), * Compared to control #, *p<0.05, ##, p<0.005, ###,*p<0.0005.

As shown in the Figures, both sitagliptin or sitagliptin monohydrate phosphate were equally effective in inhibiting viral replication and inflammatory cytokine production.

Example 5—Synthesis of Sitagliptin-Loaded Linoleic Acid Liposomal Nanoparticles Sitagliptin-loaded liposomes, with encapsulated Linoleic acid on the lipid bilayer were prepared using thin-film hydration method. Briefly, hydrogenated L-α phosphatidylcholine (PC), cholesterol and Linoleic Acid (LA) at a ratio of 6:1:3 (wt/wt) were dissolved in methanol: chloroform mixture (1:2 v/v). The solvent was removed using rotary evaporation. To completely remove the organic solvents a stream of argon was applied for 10 minutes. The thin film was hydrated with 50 mg/ml Sitagliptin phosphate monohydrate solution in dH20 (adjusted at 300 mOsm with NaCl, pH 7.4) at 40° C. The size of the particles was reduced using probe sonication until they became clear and centrifuged (12,000 rpm, 10 min) in order to precipitate and discard large liposome aggregates and titanium particles that leaked from the probe. Finally, liposome dispersions were incubated for 1 h at 40° C. in order to anneal structural defects. After annealing, the nonencapsulated Sitagliptin was separated by Size Exclusion Chromatography (Sephadex G-50 fine column). To determine the sitagliptin-lipid ratio of the liposomal formulation, sitagliptin was extracted in Chloroform:Water (1:1 v/v) biphasic system. The amount of sitagliptin in the aqueous phase (encapsulated sitagliptin) was determined by UV absorption at 270 nm. The lipid concentration was estimated using Stewart assay. The final ratio for PC:Sitagliptin was found to be PC:Sitagliptin 63:25 (wt/wt). Particle size was measured by dynamic light scattering (DLS, Malvern Nano-Z) at 25° C. at a 173° angle.

Example 6—Effects of Linoleic Acid Liposomal Nanoparticles and Sitagliptin in SARS CoV-2 Infected Mice The mice were intranasally infected with SARS CoV2 (100 k PFU), on Day 0 and treated with PBS (control), Linoleic acid liposomes (L-lipo), and liposome encapsulating sitagliptin (L-lipo+sita)—25 ug/1 mg/kg for 5 days and sacrificed on day 7. (A) Histograms showing mRNA expression level of SARS CoV 2 N protein, S Protein, assessed by qPCR, from RNA samples isolated from lung and brain samples from CoV2 infected hACE2 mice and samples were collected 7 days post infection, Mock—UV inactivated virus, Data expressed as mean±SEM, n=3, * Compared to Mock, # Compared to Mock *p<0.05, p<0.005, ###, *p<0.0005. (B) The tissues were cryosectioned and Periodic acid-Schiff staining was performed, scale bar—Top panel 100 u, bottom panel 20 u.

As shown in the Figures, sitagliptin encapsulated liposomal nanoparticles significantly inhibited viral replication and S-protein expression as shown by qPCR, and reduced mucous production as shown by Periodic acid Schiff staining of lung sections.

Example 7—Treatment of CoV-2 Infection with Sitagliptin (Prophetic)

A 55 year old female patient presents with headache, cough, and loss of taste and smell. The patient is considered obese and has Type 2 diabetes. A diagnosis of CoV-2 infection is confirmed. The patient is orally administered a therapeutically effective amount of a sitagliptin composition for a time period sufficient to alleviate the symptoms. The patient is retested twice over a several week timespan and tests negative for the virus.

Example 8—Prophylactic Treatment of CoV-2 Infection with Sitagliptin (Prophetic)

A 32 year old male patient tests negative for COVID-19 and is administered a therapeutically effective amount of a sitagliptin composition. The patient is considered obese and has Type 2 diabetes. The patient is exposed to the CoV-2 virus through contact with multiple people infected with the virus. The patient does not develop a CoV-2 infection as confirmed by testing.

Example 9—Treatment of CoV-2 Infection with Sitagliptin-Loaded Linoleic Acid Liposomal Nanoparticles (Prophetic)

A 30 year old male patient presents with coughing, headache, nausea, and vomiting. The patient is considered obese and has Type 2 diabetes. A diagnosis of CoV-2 infection is confirmed. The patient is orally administered a therapeutically effective amount of a nanosystem composition comprising a plurality of linoleic acid nanoparticles encapsulating a therapeutically effective amount of sitagliptin for a time period sufficient to alleviate the symptoms. The patient is retested twice over a several week span and tests negative for the virus.

A 55 year old male patient presents with loss of smell and taste and coughing. The patient is considered obese and has Type 2 diabetes. A diagnosis of CoV-2 infection is confirmed. The patient is orally administered a therapeutically effective amount of a nanosystem composition comprising a plurality of linoleic acid nanoparticles encapsulating a therapeutically effective amount of sitagliptin and metformin for a time period sufficient to alleviate the symptoms. The patient is retested twice over a several week span and tests negative for the virus.

Example 10—Prophylactic Treatment of CoV-2 Infection with Sitagliptin-Loaded Linoleic Acid Liposomal Nanoparticles (Prophetic)

A 45 year old female patient tests negative for COVID-19 and is administered a therapeutically effective amount of a nanosystem composition comprising a plurality of linoleic acid nanoparticles encapsulating a therapeutically effective amount of sitagliptin. The patient is considered obese and has Type 2 diabetes. The patient is exposed to the CoV-2 virus through contact with multiple people infected with the virus. The patient does not develop a CoV-2 infection as confirmed by testing.

A 50 year old female patient tests negative for COVID-19. The patient is considered obese and has Type 2 diabetes. The patient is administered a therapeutically effective amount of a nanosystem composition comprising a plurality of linoleic acid nanoparticles encapsulating a therapeutically effective amount of sitagliptin and metformin. The patient is exposed to the CoV-2 virus through contact with multiple people infected with the virus. The patient does not develop a CoV-2 infection as confirmed by testing.

CONCLUSION

The inventors find that DPP4 inhibitors, and in particular dual ACE2/DPP4 inhibitors such as sitagliptin, can treat, including prophylactically, coronavirus infection from SARS CoV-2 in obese and diabetic patients. The diabetic drug metformin also shows efficacy for treatment of COVID-19. Encapsulation of a single or combination of therapeutic agents in a linoleic acid nanoparticle provides an effective delivery vehicle above administration of the therapeutic agent(s) alone.

The disclosures of all publications cited above are expressly incorporated herein by reference, each in its entirety, to the same extent as if each were incorporated by reference individually.

It is also to be understood that the following claims are intended to cover all of the generic and specific features of the invention herein described, and all statements of the scope of the invention which, as a matter of language, might be said to fall there between. Now that the invention has been described,

What is claimed is:

1. A nanosystem targeting a severe acute respiratory syndrome coronavirus 2 (SARS COV-2) virus comprising:

at least one nanoparticle having at least one targeting moiety to form a targeted nanoparticle wherein the targeting moiety is a fatty acid selected from the group consisting of linoleic acid (LLA) and linolenic acid (LNA) wherein the targeting moiety is encapsulated in a lipid bilayer of the nanoparticle; and a therapeutic agent encapsulated within the at least one targeted nanoparticle wherein the therapeutic agent is sitagliptin;

wherein the targeting moiety binds to the CoV-2 spike protein or ACE2-spike interface of the SARS COV-2 virus.

2. The nanosystem of claim 1, wherein the nanosystem is created using a thin film hydration method.

3. The nanosystem of claim 1, wherein the targeting moiety is linoleic acid.

* * * * *